US011868581B2

(12) United States Patent
McLaughlin et al.

(10) Patent No.: US 11,868,581 B2
(45) Date of Patent: Jan. 9, 2024

(54) REMOVABLE TOUCH PANEL FOR REMOTE CONTROL AND REMOTE IMAGING IN AN ULTRASOUND IMAGING SYSTEM

(71) Applicant: Shenzhen Mindray Bio-Medical Electronics Co., Ltd., Shenzhen (CN)

(72) Inventors: Glen W. McLaughlin, San Carlos, CA (US); Barbara Makarich, Sylvania, OH (US)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 812 days.

(21) Appl. No.: 16/814,533

(22) Filed: Mar. 10, 2020

(65) Prior Publication Data
US 2020/0330073 A1    Oct. 22, 2020

Related U.S. Application Data

(60) Provisional application No. 62/836,351, filed on Apr. 19, 2019.

(51) Int. Cl.
*G06F 3/048*  (2013.01)
*G06F 3/0481*  (2022.01)
*A61B 8/00*  (2006.01)

(52) U.S. Cl.
CPC ............ *G06F 3/0481* (2013.01); *A61B 8/465* (2013.01); *A61B 8/467* (2013.01); *A61B 8/464* (2013.01)

(58) Field of Classification Search
CPC .... G06F 3/0481; G06F 3/0488; G06F 1/1632; A61B 8/465; A61B 8/467; A61B 8/464;
(Continued)

(56) References Cited

U.S. PATENT DOCUMENTS 6,475,146 B1* 11/2002 Frelburger ............... A61B 8/56
600/437
2006/0068834 A1* 3/2006 Jones .................. G01S 7/52084
455/557

(Continued)

*Primary Examiner* — Aleksey Olshannikov
(74) *Attorney, Agent, or Firm* — Kory D. Christensen

(57) ABSTRACT

An ultrasound imaging system includes an ultrasound transducer configured to transmit ultrasound waves into an exam site and receive therefrom echo signals; an image processor configured to generate an ultrasound image from the received echo signals; a primary display configured to display the ultrasound image generated by the image processor; and a removable touch panel comprising a secondary display configured to display a first graphical user interface comprising controls for accessing a first set of functions of the ultrasound imaging system while the removable touch panel is docked with the ultrasound imaging system. In one embodiment, the removable touch panel, in response to being undocked from the ultrasound imaging system, is configured to automatically replace the first graphical user interface with a second graphical user interface optimized for remote control of ultrasound imaging system, wherein the second graphical user interface comprises a display area configured to display the generated ultrasound image and a control area comprising controls for accessing a second set of functions of the ultrasound imaging system.

19 Claims, 5 Drawing Sheets

(58) Field of Classification Search
CPC ......... A61B 8/56; A61B 8/4405; A61B 8/462; A61B 8/44; A61B 8/4483; A61B 8/461; A61B 8/54
See application file for complete search history.

(56) References Cited

U.S. PATENT DOCUMENTS

| | | | |
|---|---|---|---|
| 2008/0161688 A1* | 7/2008 | Poland | G01S 7/52084 600/437 |
| 2010/0010330 A1* | 1/2010 | Rankers | G16H 15/00 600/365 |
| 2016/0350503 A1* | 12/2016 | Jun | A61B 8/465 |
| 2018/0021025 A1* | 1/2018 | Uno | G16H 50/20 600/437 |
| 2020/0281565 A1* | 9/2020 | Yee | A61B 8/465 |

* cited by examiner

REMOVABLE TOUCH PANEL FOR REMOTE CONTROL AND REMOTE IMAGING IN AN ULTRASOUND IMAGING SYSTEM

CROSS-REFERENCE TO RELATED APPLICATIONS

This application claims the benefit of U.S. Provisional Application No. 62/836,351, filed Apr. 19, 2019, for REMOVABLE TOUCH PANEL FOR REMOTE CONTROL AND REMOTE IMAGING IN AN ULTRASOUND IMAGING SYSTEM, which is incorporated herein by reference in its entirety.

TECHNICAL FIELD

The present disclosure relates to ultrasound imaging and, more specifically, to a removable touch panel for remote control and remote imaging in an ultrasound imaging system.

BACKGROUND

Operators of ultrasound imaging systems have continuously suffered from having to either move a large, cart-based system to keep it in arm's reach when performing complicated scans or forego being able to make adjustments. Most complicated exams tend to involve difficult-to-image patients that usually require a significant amount of image parameter manipulation in order to obtain high-quality diagnostic images. At the same time, such exams often require an operator to move to different locations around the patient, sometimes resulting in the exam table or other obstacles preventing access to the user interface of the ultrasound imaging system.

SUMMARY

The present disclosure provides an ultrasound imaging system including a removable touch panel that allows a clinician to remotely control the ultrasound imaging system and make parameter adjustments even when the clinician is out of arm's reach of the system.

According to one aspect, an ultrasound imaging system includes an ultrasound transducer configured to transmit ultrasound waves into an exam site and receive therefrom echo signals; an image processor configured to generate an ultrasound image from the received echo signals; a primary display configured to display the ultrasound image generated by the image processor; and a removable touch panel comprising a secondary display configured to display a first graphical user interface comprising controls for accessing a first set of functions of the ultrasound imaging system while the removable touch panel is docked with the ultrasound imaging system.

In one embodiment, the removable touch panel, in response to being undocked from the ultrasound imaging system, is configured to automatically replace the first graphical user interface with a second graphical user interface optimized for remote control of ultrasound imaging system, wherein the second graphical user interface comprises a display area configured to display the generated ultrasound image and a control area comprising controls for accessing a second set of functions of the ultrasound imaging system.

In some embodiments, the second set of functions is a subset of the first set of functions. Alternatively, the second set of functions includes one or more functions not included in the first set of functions.

In certain embodiments, the ultrasound imaging system includes a hard key interface comprising controls for accessing a third set of functions of the ultrasound imaging system. The second set of functions accessed by the second graphical user interface may include at least one function from the third set of functions accessed by the hard key interface. In one embodiment, the removable touch panel, in response to being undocked, adds at least one control to the second graphical user interface that accesses at least one respective function of the third set of functions accessed by the hard key interface. Alternatively, or in addition, the removable touch panel, in response to being undocked, configures the second graphical user interface to access, in response to a multi-touch gesture, at least one function from the third set of functions accessed by the hard key interface.

In some embodiments, at least one function from the second set of functions is selected from the group consisting of a scan mode selection function, a save image function, an annotate image function, and a measurement function. The scan mode selection function may select an active scan mode from the group consisting of a brightness mode (B-mode), color Doppler mode (CD-mode), pulsed wave mode (PW-mode), and a motion mode (M-mode). In one embodiment, at least one function of the second set of functions is selected from the group consisting of a scale adjustment function and a baseline function. In still other embodiments, the second set of functions is limited or restricted to one more of a scan mode selection function, a save image function, an annotate image function, and a measurement function.

According to one embodiment, the display area of the remote touch panel is configured to display a live streaming representation of the ultrasound image being displayed on the primary display.

In various embodiments, the removable touch panel is a sterilizable, sealed unit. The removable touch panel may be configured to receive a wireless power transfer from the ultrasound imaging system while docked. In some embodiments, the wireless power transfer is performed by induction. The removable touch panel may be configured to detect an undocking event in response to interruption of a wireless power transfer.

In some embodiments, the removable touch panel further comprises a proximity detector configured to determine whether the removable touch panel is within a particular distance of the ultrasound imaging system. The removable touch panel may further comprises a speaker configured to generate an alarm if the removable touch panel is moved beyond the particular distance.

In one embodiment, the removable touch panel further comprises a security lock configured to disable the removable touch panel if it is moved beyond the particular distance. The proximity detector may be configured to use one or more of wireless signal strength or global positioning to determine whether the removable touch panel is within the particular radius of the ultrasound imaging system.

According to another aspect, a method performed by an ultrasound imaging system includes transmitting, via an ultrasound transducer, ultrasound waves into an exam site and receiving therefrom echo signals; generating, via an image processor, an ultrasound image from the received echo signals; displaying the ultrasound image generated by the image processor on a primary display; detecting a removable touch panel being undocked from the ultrasound imaging system, the removable touch panel comprising a secondary display configured to display a first graphical user interface including controls for accessing a first set of functions of the ultrasound imaging system while the removable touch panel is docked with the ultrasound imaging system.

In one embodiment, the method further includes automatically replacing the first graphical user interface on the removable touch panel with a second graphical user interface optimized for remote control of ultrasound imaging system, wherein the second graphical user interface comprises a display area configured to display the generated ultrasound image and a control area including controls for accessing a second set of functions of the ultrasound imaging system, wherein the second set of functions comprises at least a subset of the first set of instructions.

In some embodiments, automatically replacing the first graphical user interface with the second graphical user interface comprises adding to the second graphical user interface at least one control for accessing the at least one function from the third set of functions. Alternatively, or in addition, automatically replacing the first graphical user interface with the second graphical user interface comprises configuring the second graphical user interface to access, in response to a multi-touch gesture, the at least one function from the third set of functions accessed by the hard key interface.

In certain embodiments, automatically replacing the first graphical user interface with the second graphical user interface comprises removing from the second graphical user interface at least one control provided in the first graphical user interface. Alternatively, or in addition, automatically replacing the first graphical user interface with the second graphical user interface comprises configuring the second graphical user interface to display a live streaming representation of the ultrasound image being displayed on the primary display.

In one embodiment, detection of whether the removable touch panel has been undocked comprises detecting interruption of a wireless power transfer between the ultrasound imaging system and the removable touch panel.

The method may further include detecting, via a proximity detector, whether removable touch panel is within a particular distance of the ultrasound imaging system, and generating an alarm if removable touch panel is moved beyond the particular distance. Alternatively, or in addition, the method may include detecting, via a proximity detector, whether removable touch panel is within a particular distance of the ultrasound imaging system, and disabling at least one feature of the removable touch panel if it is moved beyond the particular distance.

In still another aspect, a computer readable medium comprises program code that, when executed by a processor, cause the processor to perform a method comprising: generating an ultrasound image from echo signals received from an ultrasound transducer; displaying the ultrasound image generated by the image processor on a primary display; detecting a removable touch panel being undocked from the ultrasound imaging system, the removable touch panel comprising a secondary display configured to display a first graphical user interface including controls for accessing a first set of functions of the ultrasound imaging system while the removable touch panel is docked with the ultrasound imaging system; and automatically replacing the first graphical user interface on the removable touch panel with a second graphical user interface optimized for remote control of ultrasound imaging system, wherein the second graphical user interface comprises a display area configured to display the generated ultrasound image and a control area including controls for accessing a second set of functions of the ultrasound imaging system, wherein the second set of functions comprises at least a subset of the first set of instructions.

DETAILED DESCRIPTION

Figure 1:
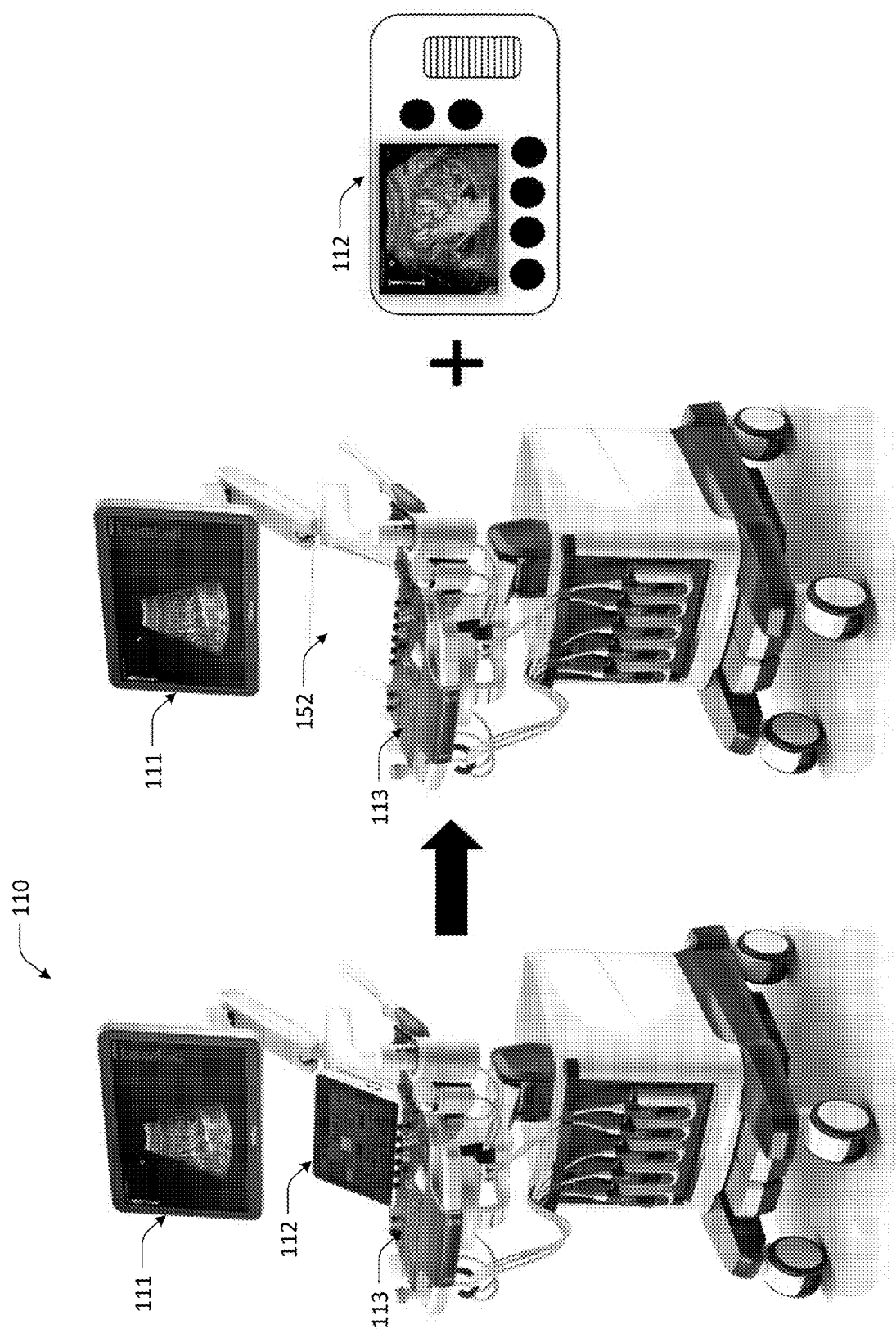
FIG. 1 illustrates an ultrasound imaging system with a removable touch panel in a docked state and an undocked state.

Disclosed herein are embodiments of an ultrasound imaging system including a removable touch panel that can be undocked during an exam and used to make parameter adjustments and remotely control the ultrasound imaging system.

In one embodiment, the removable touch panel communicates with the ultrasound imaging system in a wireless manner and also reconfigures its overall functionality and layout when undocked to enable the operator to control the system in an optimized manner even though they are not within arm's reach of the system. The removable touch panel may display a graphical user interface including a live display of the ultrasound image being generated, as well as select group of controls for carrying out an exam, including controls for changing an active scan mode, saving an image, annotating an image, measuring features of an image.

Once docked with the system, the touch panel may revert back to a configuration optimized for operation where additional user interface capabilities are available. Furthermore, while docked, the touch panel may be wirelessly recharged by the system via induction or RF transmission.

Merely providing a touch panel (removable or not) in an ultrasound imaging system is not sufficient to provide the necessary controls for the clinician to efficiently operate the ultrasound platform, as the layout, controls, and structure of the touch panel when connected to the main system will normally be optimized in work in conjunction with the rest of the system's user interface and not in a stand-alone manner. In order to satisfy the clinician's needs for the removable touch panel, the controls, layout and functionality are modified in various embodiments when used in a remote manner. These modifications, for example, may include displaying the ultrasound image on the touch panel, the ability to change modes on the system and control each mode, save an image, make measurements, and/or annotate the image.

As explained in greater detail below, some functionality and/or options that may not need to be available on the removable touch panel may include, for example, the ability to change the transducer, service options, DICOM (Digital Imaging and Communications in Medicine) options, archival options, and the like. The main focus of the touch panel while operating in a remote manner is to enable the operator to have a quick, simple, and efficient platform to make the necessary adjustments, measurements, annotations and storage of images when working at a distance longer than arm's length from the main ultrasound imaging system.

The standard workflow for when a clinician may be working at a distance longer than an arm's length from the ultrasound imaging system may include, for example, lower extremity venous studies, difficult abdominal studies, interventional procedures, any sterile procedure, and the like. All of these procedures typically require an operator to reposition a bulky, cart-based ultrasound imaging system, interfering with the operator's ability to make adjustments. Both of these scenarios seriously impact the operator's workflow by either adding time to the exam or having the operator accept that they are obtaining suboptimal images.

In one embodiment, the removable touch panel is completely sealed and sterilizable, given that the touch panel may need to be used within the sterile field during operating procedures. As such, power transmission and interfacing with the main ultrasound imaging system may be accomplished wirelessly. For example, inductive coupling may be used to transfer power when the touch panel is docked in the main ultrasound unit. In other embodiments, RF transmission could be used. However, for close proximity, inductive coupling is more efficient in transferring power.

Communication with the system may be accomplished via Wi Fi communication or other similar protocols as the bandwidth requirements of this path require the touch panel to be able to receive video signals. Current protocols that would be sufficient may include a number of the 802.11 protocols, as these offer a balance between performance and power.

In one embodiment, the touch panel may be able to detect whether it is docked or undocked, such that when it is undocked, the touch panel can automatically reconfigure the user interface without the need for the clinician to perform any additional steps. In one embodiment, the system is able to use the charging state of an inductive power transfer from the main ultrasound imaging system to the touch panel, such that when this link is broken, the touch panel is no longer in a docked state and will automatically convert to the desired standalone configuration.

A concern that most hospitals have with removable items of equipment is that they are easily misplaced or stolen. In order to reduce this problem, the Wi Fi signal strength may be monitored by the touch panel and the main ultrasound imaging system so that when the touch panel is moved more than a particular distance from the system, an alarm may be sounded to inform the operator that they need to return the touch panel to a docking configuration with the system. In another embodiment, the touch panel may become non-functional after a certain amount of time until it is docked back into the host ultrasound imaging system to reestablish the link between the two devices. In addition, using Wi Fi, Cellular, and GPS capabilities, additional security measurements may be taken for the touch panel to broadcast its location to a secure site so that it can be tracked.

Referring now to FIG. 1, there is shown ultrasound imaging system 110 in which a removable touch panel 112 is shown in both a docked state, as shown on the left of the arrow, and an remote (undocked) state, as shown on the right. As described more fully below, the touch panel 112 enables a contextual set of controls based on which operating mode the touch panel 112 is in (i.e., docked or remote).

The ultrasound imaging system 110 may further include a relatively larger fixed display 111 that is used to show ultrasound images in one or both operating modes. The ultrasound imaging system 110 may also include a "hard" key interface 113 comprising a variety of physical keys and controls, including buttons, knobs, sliders, and the like. The hard key interface 113 enables the operator to control the ultrasound imaging system 110 by feel. Once becoming familiar with the layout, the operator can often use it without needing to look at the hard key interface 113.

In one embodiment, the ultrasound imaging system 110 may be transformed, as shown on the right side of FIG. 1, such that the touch panel 112 can operate the system 110 remotely as well as display the current ultrasound image. When operating the ultrasound imaging system 110 in a remote manner, the physical system 110 remains very similar, as there is still the fixed display 111 for displaying ultrasound images, as well as the hard key interface 113. However, the touch panel 112 is shown as being removed from a docking area 152 and is now used as a separate controller, wirelessly communicating with the ultrasound imaging system 110.

In one embodiment, when the touch panel 112 is undocked from the ultrasound imaging system 110, it may reconfigure its screen layout and controls so it is optimized to operate the ultrasound imaging system 110 in a remote manner as well as provide the operator with the necessary feedback so they are not required to be looking at the ultrasound imaging system 110 as well.

Figure 2:
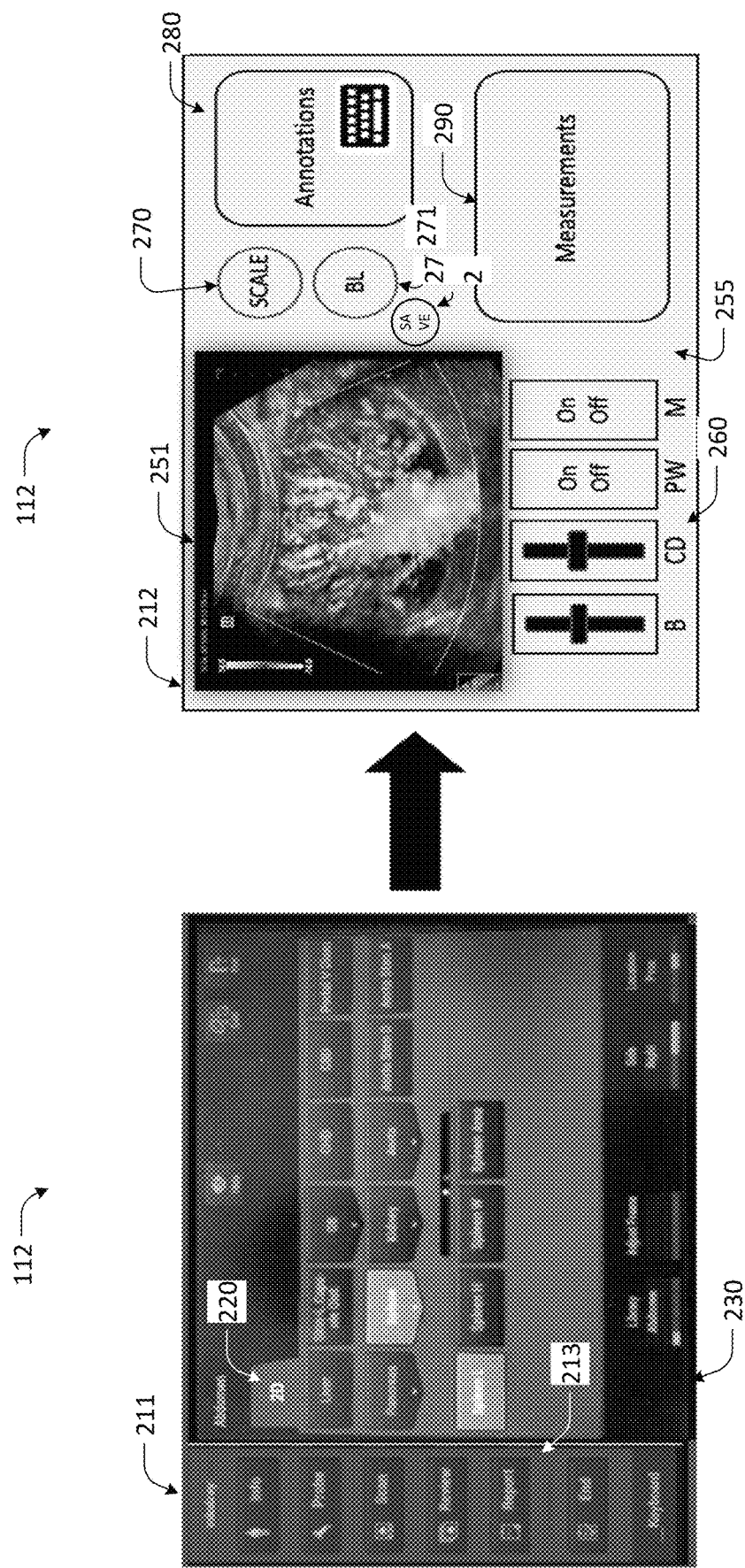
FIG. 2 illustrates reconfiguration of a graphical user interface from the docked state to the undocked state.

FIG. 2 illustrates how a graphical user interface of the touch panel 112 may be reconfigured when transitioning from a docked state (as shown on the left side of the arrow) to an undocked state (as shown on the right). In one or both states, the touch panel 112 may function as a secondary display for the ultrasound imaging system, which includes the ability to display the ultrasound image, as well as various controls for operating the ultrasound imaging system.

The left side of FIG. 2 illustrates a first graphical user interface 211 suitable for when the touch panel 112 is docked with the main ultrasound imaging system (not shown). The first graphical user interface 211 may be optimized for use in conjunction with the hard key interface 113 of FIG. 1, such that some functions accessed by the hard key interface 113 need not be available (or may be less accessible) in the docked state. Furthermore, the first graphical user interface 211 may provide access to advanced and/or lesser-used functions, including changing the transducer, service options, DICOM (Digital Imaging and Communications in Medicine) options, archival options, and the like.

For example, on the first graphical user interface 211, a region 213 to quickly access a number of various categories of options may be provided. These categories allow quick access to the general items an operator may want to do when configuring, scanning, reviewing, generating a report or closing out an exam. All of these categories are "non-scanning" items except for the scan category. When in the scan category, the operator may have access to extended, seldom used controls to adjust various imaging modes as well as potentially enable new modes. When in the 2D mode 220, for example, and the operator wants to annotate an image, they can quickly select a number of standard pre-typed words like Spleen L, 221, to make their workflow more efficient. Various additional contextual menus 230 may also be provided based on the currently-selected options.

When the touch panel 112 is undocked from the ultrasound imaging system 110, the use model may shift from a method to enhance the overall usability of the system 110 to that of a more limited functioning, stand-alone touch-driven ultrasound controller that the operator can control the ultrasound imaging system 110 as well as view a live ultrasound image in a remote manner.

As shown on the right side of the arrow in FIG. 2, the undocked graphical user interface 212 may display the live ultrasound image in a display area 251, along with a set of basic controls in a control area 255. The basic controls may include scan mode controls 260 for adjusting the active scan mode, e.g., brightness mode (B-mode), color Doppler mode (CD-mode), pulsed wave mode (PW-mode), and motion mode (M-mode). The basic controls may also include a control 270 for adjusting the scale, a control 271 for adjusting the baseline (BL), a control 280 for annotating the image, and a control 290 for performing various measurements of features of the ultrasound image. In one embodiment, a specific control 272 may be provided for saving an image, although, in other embodiments, the save function may be implemented via a gesture (as described below) or in conjunction with another function, such when a captured image is annotated.

Various other controls (not shown) may be included for more advance activities that may need to be done in a remote manner, such as CEUS (Contrast-enhanced ultrasound). Some of the controls, such as the scale 270 and baseline 271 controls are contextually active and may only be displayed, for example, in CD-mode.

In one embodiment, some basic ultrasound controls, such as freeze/unfreeze, scroll back and forth, store, clip, etc., may be entered using the touch panel 112 via multi-touch/gesture-type motions. For example, the operator may tap the active display area 251 (and/or control area 255) to freeze/unfreeze. Likewise, the operator may drag a finger left or right on the display to scroll backward or forward, respectively.

In operation, the graphical user interface 211 may provide controls for accessing a first set of functions of the ultrasound imaging system 110 while the removable touch panel 112 is docked with the ultrasound imaging system 110. In response to being undocked, the removable touch panel 112 may be configured to automatically replace the first graphical user interface 211 with the second graphical user interface 212 optimized for remote control of ultrasound imaging system 110. As noted, the second graphical user interface may include the display area 251 configured to display the generated ultrasound image, as well as the control area 255 comprising controls for accessing a second set of functions of the ultrasound imaging system while the touch panel 112 is undocked. Of course, the display area 251 and control area 255 may overlap or be co-extensive.

In one embodiment, the second set of functions available when undocked is a limited subset of the first set of functions. However, in another embodiment, the second set of functions includes one or more functions not included in the first set of functions. For example, in some embodiments, the hard key interface 113 (not shown) may provide controls for accessing a third set of functions of the ultrasound imaging system 112, and the second set of functions accessible in the undocked mode may include at least one function from the third set of functions accessed by the hard key interface 113.

In one embodiment, the removable touch panel 112, in response to being undocked, adds at least one control to the second graphical user interface that accesses at least one respective function of the third set of functions accessed by the hard key interface. Alternatively, or in addition, the removable touch panel, in response to being undocked, configures the second graphical user interface to access, in response to a multi-touch gesture, at least one function from the third set of functions accessed by the hard key interface 113.

The second set of functions accessed in undocked mode may be selected from the group consisting of a scan mode selection function, a save image function, an annotate image function, and a measurement function. In certain embodiments, the second set of functions may contextually include a scale adjustment function and/or a baseline function.

In certain embodiments, the second set of functions accessible in undocked mode is limited or restricted to a scan mode selection function, a save image function, an annotate image function, and/or a measurement function. In other words, for simplicity and ease of use, some of the functions accessible in the docked graphical user interface 211 may not be available so as to not complicate or clutter the second graphical user interface 212.

In one embodiment, the display area 251 of the remote touch panel 112 is configured to display a live streaming representation of the ultrasound image being displayed on the primary display 111. The live streaming representation may be sent using various protocols, such as MPEG-DASH, HTTP Live Streaming (HLS), Smooth Streaming, and HDS, although various other protocols and techniques may be used.

Figure 3:
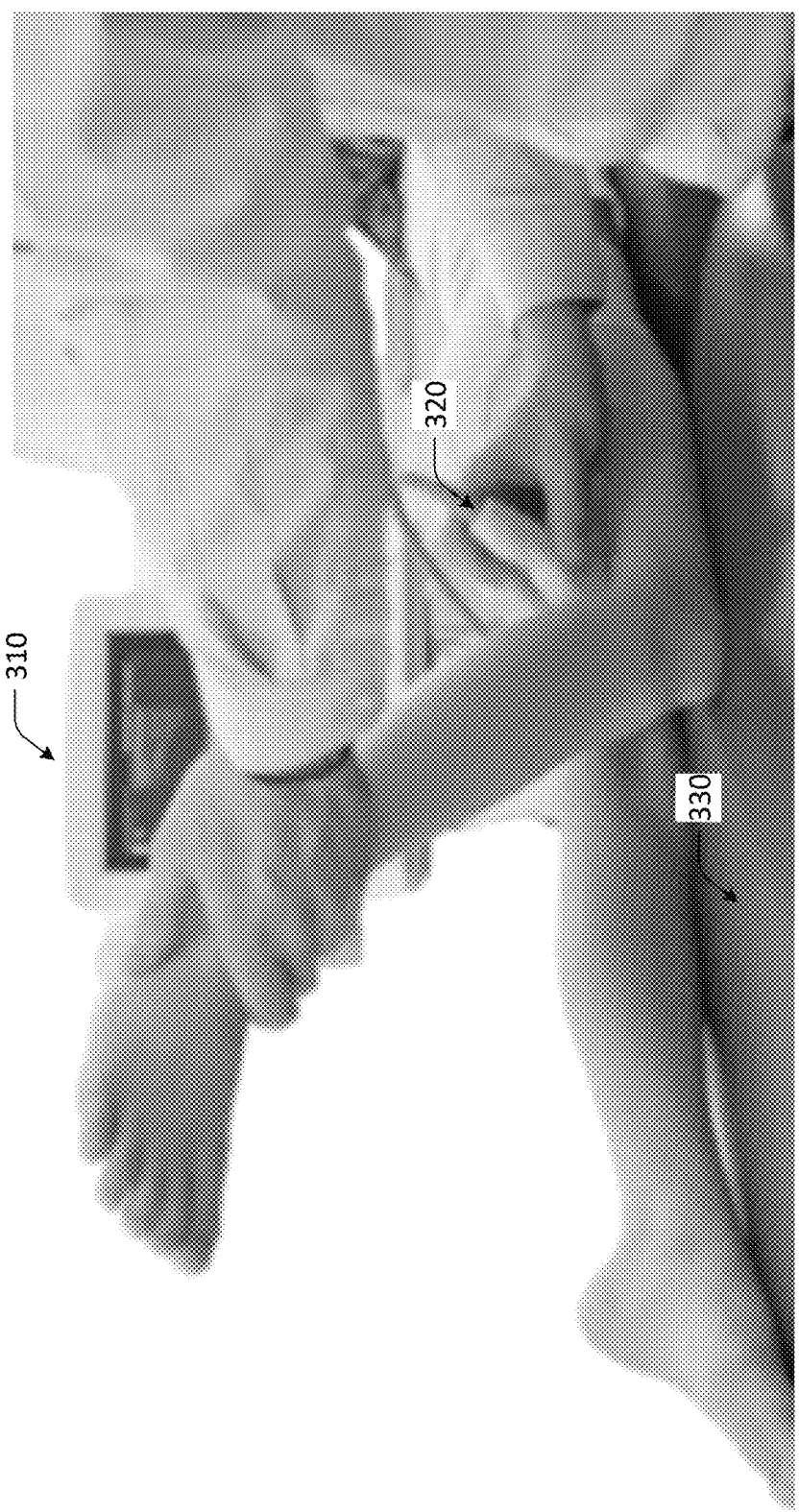
FIG. 3 illustrates a traditional workflow for an ultrasound exam when the operator is out of arm's reach of the ultrasound imaging system.

FIG. 3 illustrates a traditional ultrasound imaging system workflow when the operator needs to work at greater than arm's length from the ultrasound imaging system. In the standard workflow, there is an ultrasound imaging system, 310, that is at a sufficient distance from the operator that they are incapable of making any adjustments. A transducer 320 is connected to the ultrasound imaging system 310, which the operator uses for imaging the area under observation. A number of systems will offer some limited controls via a foot switch for example freeze and store but this is of minimal value as the operator typically needs to make additional image adjustments, and as such, requires an additional individual to be present to adjust the ultrasound imaging system. Often, the ultrasound imaging system 310 is separated from the operator via an exam table 330.

Figure 4:
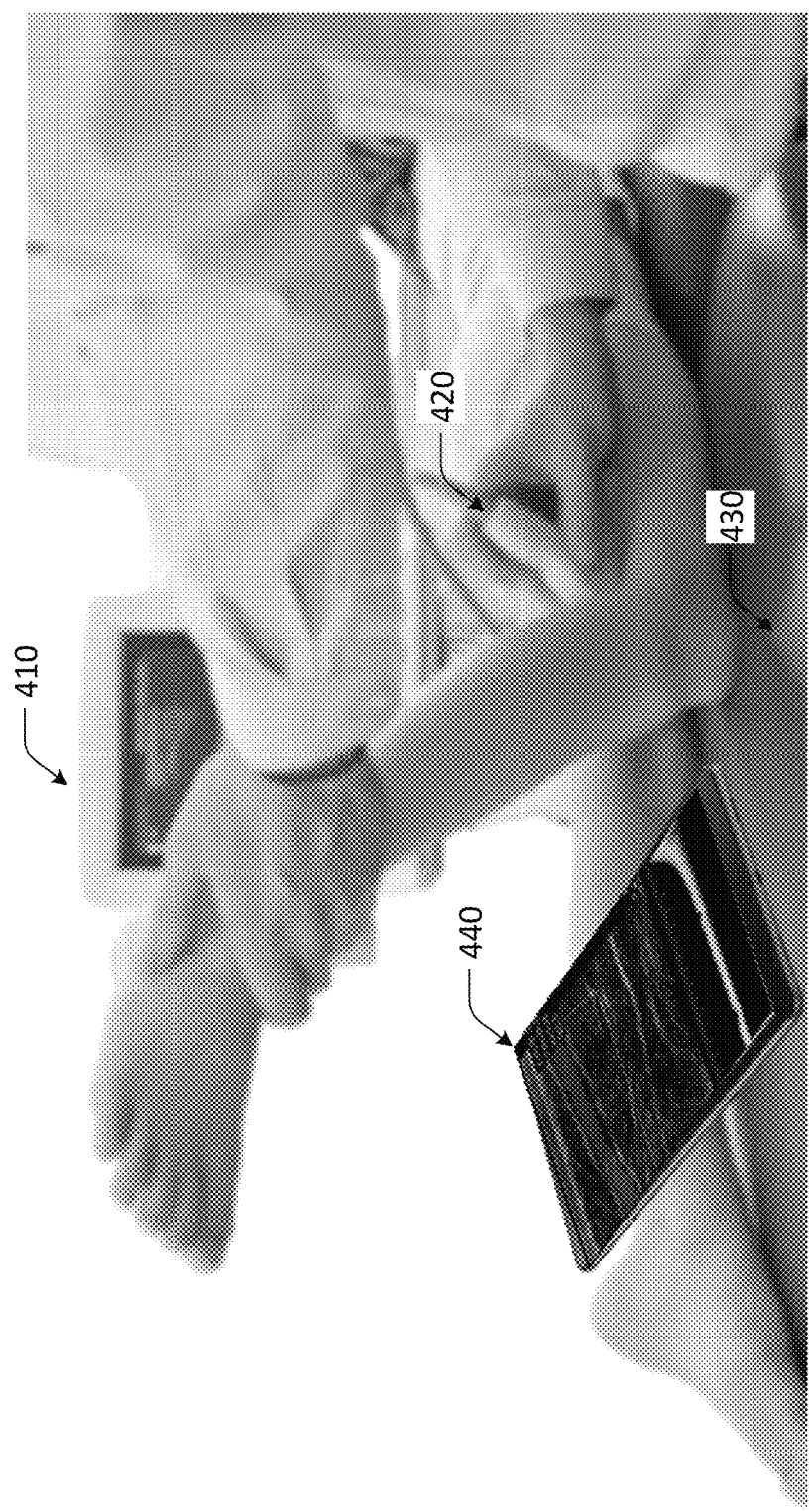
FIG. 4 illustrates a workflow in accordance with one embodiment of the present disclosure.

FIG. 4 illustrates a modified workflow according to one embodiment. In this modified workflow, there is an ultrasound imaging system 410 at a distance from the operator, such that it is impossible to make direct adjustments on the main unit. As in FIG. 3, there is a transducer 420 attached to the main ultrasound imaging system that the physician is using for the exam as well as the exam table 430 that separates the physician from the ultrasound imaging system 410.

In this workflow, a touch screen 440 (similar to the touch screen 112 of FIG. 1) is provided, which the physician can remove from the ultrasound imaging system 410 when performing an activity that requires them to work at a distance from the ultrasound imaging system 410 where they are out of reach of the main controls. This removable touch screen 440 now enables the physician to visualize not only the ultrasound imaging activities but also adjust a number of important parameters, e.g., mode changes, measurements, annotations and the like, while working in a remote manner. This significantly enhances the physician's workflow as well as the quality of the exam being performed as it ensures that the physician is able to continue to directly operate the ultrasound imaging system 410 in an optimal manner without the need for an additional individual to be controlling the ultrasound imaging system 410 and interpreting and implementing the requests of the physician.

Figure 5:
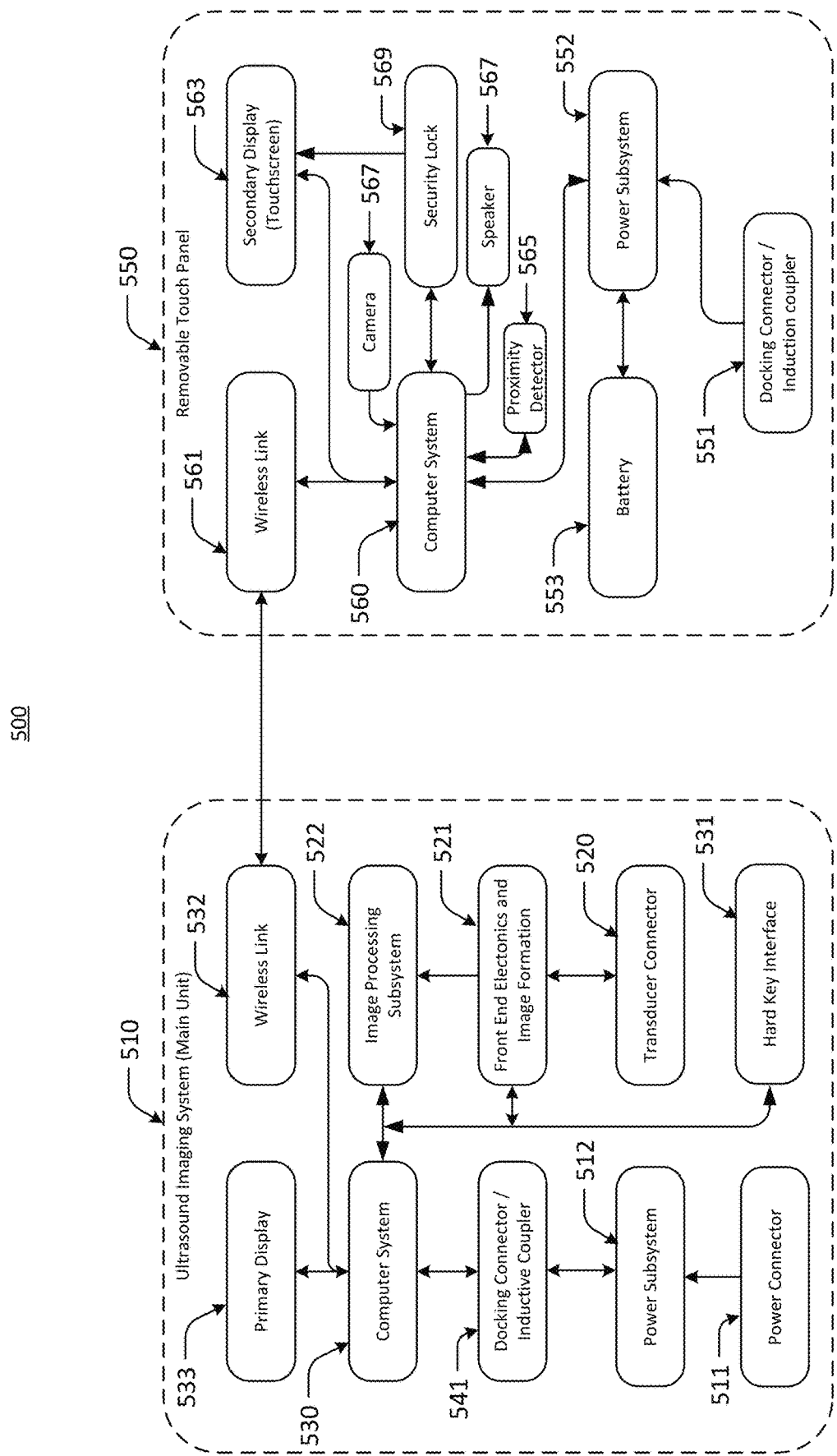
FIG. 5 is a simplified block diagram of an ultrasound imaging system with a removable touch panel.

FIG. 5 is a simplified block diagram of an ultrasound imaging system 500, including a main unit 510 and a removable touch panel 550. In FIG. 1, the main unit 510 is referred to as ultrasound imaging system 110. In the following discussion, however, the main unit 510 and removable touch panel 550 are conceptually components of an overall system 500, in which the removable touch panel 550 may be used in both a docked and undocked configuration.

As illustrated, the main unit 510 may include a power connector 511 to provide access to an electrical power source, as well as a power subsystem 512 for distributing power to all the various systems within the main unit 510. In one embodiment, a transducer connector 520 is provided to enable various types of transducers to be connected to the main unit 510, including linear probes, curvilinear robes, and phased array probes. The transducer 520 transmits ultrasonic waves into human tissue under examination and receives echo signals therefrom, which are converted into electric signals.

The transducer connector 520 interfaces with front end electronics and image formation circuitry 521 to both transmit and receive the signals and process the signals from the transducer into a formed image. This formed image is than passed to an image processing subsystem 522 where is processed so that it is formatted correctly for display. Collectively, the front end electronics and image formation circuitry 521 and image processing subsystem 522 may be referred to as an image processing system or image processor, since it is focused on generating images from received ultrasound echo signals. The process may be controlled and/or monitored by a computer system 530 (including a processor, memory, I/O devices, and the like). Conventional techniques for generating an ultrasound image are understood to a person of ordinary skill in the art and will not be described in detail here.

From the computer system 530, the formed image may be rendered on a primary display 533 or transmitted via a wireless link 532 so that the removable touch panel 550 can receive and display the formed image while undocked. The computer system 530 may receive and process inputs from a hard key interface 531, similar to the hard key interface 113 shown in FIG. 1, which controls various functions of the main unit 510.

The computer system 530 may also receive user inputs from the removable touch panel 550 via the wireless link 532 in both the docked and undocked configurations. In such a way, the removable touch panel 550 may provide a supplemental user interface for a wide range of functions main unit 510 while docked therewith. Alternatively, when the removable touch panel 550 is undocked, it may provide access to an optimized interface for remotely controlling the main unit 110 during an examination.

The main unit 510 may further include a docking connector/inductive coupler 541 to enable power transfer between the main unit 510 and the removable touch panel 550. In one embodiment, the power transfer may be wireless, although various types of physical connectors could be used as known to a person of skill in the art. The docking connector/inductive coupler 531 may be integrated into the docking area 152 shown in FIG. 1. In some embodiments, a non-inductive docking connector may also be used to transfer information from the removable touch panel 550 and the main unit 510 when docked.

In one embodiment, the removable touch panel 550 has a docking connector 551 where it docks into the main unit 510 to receive power, ideally in a wireless manner as the removable touch panel 550 may be a sealed unit so that it may be easily sterilized and used in a sterile environment. The docking connector/inductive coupler 551 provides power to a power subsystem 552 that distributes power to all the other subsystems within the removal touch panel 550 along with the battery 553. The battery 553 can both receive and provide power to the power subsystem 552. The battery 553 receives power when the removable touch panel 550 is docked and provides power when the removable touch panel 550 is operated in a remote manner. The removable touch panel 550 and/or the main unit 510 may detect whether the removable touch panel 550 is in a docked or undocked state based on whether the removable touch panel 550 is receiving power from the main unit 510.

The removable touch panel 550 also includes a wireless link 561 that can receive and transmit data to the main unit 510, as well as distribute this information to a computer system 560 (including a processor, memory, and the like) for interpretation. The computer system 560 uses this information control and modify a secondary display (touchscreen) 563, such as a capacitive touchscreen. The computer system 560 also receives user input from the touchscreen 563 and interprets it to modify what is displayed on the touchscreen 563 and/or transmit information over the wireless link 561, so that the main unit 510 can make the necessary adjustments requested by the operator of the removable touch panel 550.

In one embodiment, the removable touch panel 550 includes a proximity detector 565 that determines whether the removable touch panel 550 is within a particular distance of the main unit 510 while undocked. The proximity detector 565 may be implemented as a separate component, as shown, such as a GPS chipset. Alternatively, the proximity detector 565 may be implemented as a software module executing on the computer system 560, which determines the distance of the removable touch panel 550 from the main unit 510 based, for example, on an indication of wireless signal strength provided by the wireless link 561.

In one embodiment, removable touch panel includes speaker 567 to generate an alarm if the removable touch panel is moved beyond a particular distance (radius) or where the wireless signal strength decreases to a particular threshold level. A speaker (not shown) or other indicator, such as a visible warning light, may also be included in the main unit 510 in the event that the removable touch panel 550 is carried too far from the main unit 510. This feature could also serve as a low-battery warning if the removable touch panel 550 is left undocked long enough that the battery 553 has been depleted, which the main unit 510 may detect, for example, due to a lack of communication with the removable touch panel 550.

Alternatively, if the proximity detector 565 is implemented using GPS or another method to determine an approximate physical location, the distance may be calculated based on a known (or calculated) location of the main unit 510 and the removable touch panel.

In one embodiment, the removable touch panel 550 may further include a security lock 569 that disables one or more features of the removable touch panel 550 if it is moved beyond the particular distance from the main unit 510. For example, the security lock 569 may interact with the touchscreen 563 to prevent user input and optionally display a message indicating that the removable touch panel 550 needs to be re-docked in order to resume operation.

While the embodiment shown in FIG. 5 depicts the proximity detector 565, speaker 567, and security lock 569 as being controlled by the computer system 560, those skilled in the art will understand that special-purpose hardware may be used without needing to involve the computer system 560.

In one embodiment, the removable touch panel 550 may further include a camera 571 to allow an operator to take photographs of how a patient might present and include them in the patient's medical records. Photograph data may be sent to the ultrasound imaging system 510 via the wireless link 561.

This disclosure has been made with reference to various exemplary embodiments including the best mode. However, those skilled in the art will recognize that changes and modifications may be made to the exemplary embodiments without departing from the scope of the present disclosure. For example, various operational steps, as well as components for carrying out operational steps, may be implemented in alternate ways depending upon the particular application or in consideration of any number of cost functions associated with the operation of the system, e.g., one or more of the steps may be deleted, modified, or combined with other steps.

Additionally, as will be appreciated by one of ordinary skill in the art, principles of the present disclosure may be reflected in a computer program product on a computer-readable storage medium having computer-readable program code means embodied in the storage medium. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. An ultrasound imaging system comprising:
   an ultrasound transducer configured to transmit ultrasound waves into an exam site and receive therefrom echo signals;
   an image processor configured to generate an ultrasound image from the received echo signals;
   a primary display configured to display the ultrasound image generated by the image processor; and
   a removable touch panel configured to receive power from the ultrasound imaging system when docked, the removable touch panel comprising a secondary display configured to display a first graphical user interface comprising controls for accessing a first set of functions of the ultrasound imaging system while the removable touch panel is docked with the ultrasound imaging system, wherein the controls for accessing the first set of functions include a control for changing the ultrasound transducer;
   wherein the removable touch panel, in response to the removable touch panel being undocked, is configured to automatically replace the first graphical user interface with a second graphical user interface optimized for remote control of ultrasound imaging system, wherein the second graphical user interface comprises:
      a display area configured to display the generated ultrasound image; and
      a control area comprising controls for accessing a second set of functions of the ultrasound imaging system, wherein the second set of functions is a limited subset of the first set of functions, such that the second set of functions includes some but not all of the first set of functions, wherein the controls for accessing the second set of functions does not include the control for changing the ultrasound transducer, and wherein at least a subset of the controls for accessing the second set of functions are contextually active and only displayed for a particular ultrasound imaging mode.

2. The ultrasound imaging system of claim 1, further comprising a hard key interface comprising controls for accessing a third set of functions of the ultrasound imaging system.

3. The ultrasound imaging system of claim 2, wherein the second set of functions includes at least one function from the third set of functions accessed by the hard key interface.

4. The ultrasound imaging system of claim 2, wherein the removable touch panel, in response to being undocked, adds at least one control to the second graphical user interface that accesses at least one respective function of the third set of functions accessed by the hard key interface.

5. The ultrasound imaging system of claim 2, wherein the removable touch panel, in response to being undocked, configures the second graphical user interface to access, in response to a multi-touch gesture, at least one function from the third set of functions accessed by the hard key interface.

6. The ultrasound imaging system of claim 1, wherein at least one function from the second set of functions is selected from the group consisting of a scan mode selection function, a save image function, an annotate image function, and a measurement function.

7. The ultrasound imaging system of claim 1, wherein at least one function of the second set of functions is selected from the group consisting of a scale adjustment function and a baseline function.

8. The ultrasound imaging system of claim 1, wherein the second set of functions is limited to one more of a scan mode selection function, a save image function, an annotate image function, and a measurement function.

9. The ultrasound imaging system of claim 1, wherein the display area of the removable touch panel is configured to display a live streaming representation of the ultrasound image being displayed on the primary display.

10. The ultrasound imaging system of claim 1, wherein the removable touch panel comprises a camera for capturing photographic information for transmission to the ultrasound imaging system via a wireless link for storage in a patient's examination record.

11. The ultrasound imaging system of claim 1, wherein the removable touch panel further comprises a proximity detector configured to determine whether the removable touch panel is within a particular distance of the ultrasound imaging system.

12. The ultrasound imaging system of claim 11, wherein the removable touch panel further comprises a speaker configured to generate an alarm if the removable touch panel is moved beyond the particular distance.

13. The ultrasound imaging system of claim 11, wherein the removable touch panel further comprises a security lock configured to disable the removable touch panel if it is moved beyond the particular distance.

14. The ultrasound imaging system of claim 11, wherein the proximity detector is configured to use one or more of wireless signal strength or global positioning to determine whether the removable touch panel is within the particular distance of the ultrasound imaging system.

15. The ultrasound imaging system of claim 1, wherein the particular ultrasound imaging mode for which the at least the subset of the controls are contextually active is selected from the group consisting of brightness mode (B-mode), color Doppler mode (CD-mode), pulsed wave mode (PW-mode), and motion mode (M-mode).

16. The ultrasound imaging system of claim 15, wherein the at least the subset of the controls that are contextually active includes:
at least one control for adjusting a scale; and
at least one control for adjusting a baseline.

17. The ultrasound imaging system of claim 1, wherein the controls for accessing the second set of functions lacks a control to freeze or unfreeze the display area of the removable touch panel, and wherein freezing or unfreezing the display area is performed by tapping the display area.

18. A method performed by an ultrasound imaging system, the method comprising:
transmitting, via an ultrasound transducer, ultrasound waves into an exam site and receiving therefrom echo signals;
generating, via an image processor, an ultrasound image from the received echo signals;
displaying the ultrasound image generated by the image processor on a primary display;
receiving power at a removable touch panel from the ultrasound imaging system, the removable touch panel comprising a secondary display configured to display a first graphical user interface including controls for accessing a first set of functions of the ultrasound imaging system while the removable touch panel is docked with the ultrasound imaging system, wherein the controls for accessing the first set of functions include a control for changing the ultrasound transducer;
detecting that the removable touch panel is no longer docked with the ultrasound imaging system; and
in response to detecting that the removable touch panel is no longer docked with the ultrasound imaging system, automatically replacing the first graphical user interface on the removable touch panel with a second graphical user interface optimized for remote control of the ultrasound imaging system, wherein the second graphical user interface comprises a display area configured to display the generated ultrasound image and a control area including controls for accessing a second set of functions of the ultrasound imaging system, wherein the second set of functions comprises a subset of the first set of functions, such that the second set of functions includes some but not all of the first set of functions, wherein the controls for accessing the second set of functions does not include the control for changing the ultrasound transducer, and wherein at least a subset of the controls for accessing the second set of functions are contextually active and only displayed for a particular ultrasound imaging mode.

19. A non-transitory computer readable medium comprising program code that, when executed by a processor, cause the processor to perform a method comprising:
generating an ultrasound image from echo signals received from an ultrasound transducer;
displaying the ultrasound image on a primary display;
receiving power at a removable touch panel from an ultrasound imaging system, the removable touch panel comprising a secondary display configured to display a first graphical user interface including controls for accessing a first set of functions of the ultrasound imaging system while the removable touch panel is docked with the ultrasound imaging system, wherein the controls for accessing the first set of functions include a control for changing the ultrasound transducer;
detecting that the removable touch panel is no longer docked with the ultrasound imaging system; and
in response to detecting that the removable touch panel is no longer docked with the ultrasound imaging system, automatically replacing the first graphical user interface on the removable touch panel with a second graphical user interface optimized for remote control of the ultrasound imaging system, wherein the second graphical user interface comprises a display area configured to display the generated ultrasound image and a control area including controls for accessing a second set of functions of the ultrasound imaging system, wherein the second set of functions comprises a subset of the first set of functions, such that the second set of functions includes some but not all of the first set of functions, wherein the controls for accessing the second set of functions does not include the control for changing the ultrasound transducer, and wherein at least a subset of the controls for accessing the second set of functions are contextually active and only displayed for a particular ultrasound imaging mode.

* * * * *